United States Patent
Fujii et al.

(10) Patent No.: US 6,939,897 B2
(45) Date of Patent: Sep. 6, 2005

(54) METHOD AND COMPOSITION FOR INHIBITING ARTERIOSCLEROSIS

(75) Inventors: Kenji Fujii, Kobe (JP); Taizo Kawabe, Takasago (JP); Kazunori Hosoe, Takasago (JP); Takayoshi Hidaka, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/892,164

(22) Filed: Jul. 16, 2004

(65) Prior Publication Data

US 2004/0248992 A1 Dec. 9, 2004

Related U.S. Application Data

(62) Division of application No. 10/275,553, filed as application No. PCT/JP01/03862 on May 9, 2001, now abandoned.

(30) Foreign Application Priority Data

May 9, 2000 (JP) ........................................ 2000-135569

(51) Int. Cl.[7] ..................... A61K 31/12; A61K 31/405; A61K 31/35
(52) U.S. Cl. ................. 514/690; 514/415; 514/460
(58) Field of Search ................. 514/415, 460, 514/690

(56) References Cited

U.S. PATENT DOCUMENTS 4,929,437 A * 5/1990 Tobert ..................... 424/94.1
5,082,650 A   1/1992 Folkers et al.
5,316,765 A   5/1994 Folkers et al.

FOREIGN PATENT DOCUMENTS

EP   0 383 432 B1   8/1990
EP   0 882 450 A2  12/1998

* cited by examiner

*Primary Examiner*—Raymond J. Henley, III
(74) *Attorney, Agent, or Firm*—Sughrue Mion, PLLC

(57) ABSTRACT

The present invention has for its object to provide a method and a composition for achieving a more efficient recovery of the antioxidant activity of plasma LDL, or even augmentation thereof, which has been depressed by the use of an antihyperlipidemic or cholesterol-lowering drug to thereby insure a potentiated antiarteriosclerotic efficacy. A method for inhibiting arteriosclerosis, which comprises using a combination of a cholesterol-lowering agent and a reduced coenzyme $Q_{10}$ represented by the following formula (1), and a composition for inhibiting arteriosclerosis containing both a cholesterol-lowering agent and said reduced coenzyme $Q_{10}$.

(1)

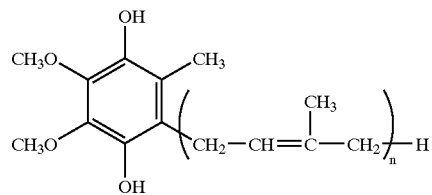

2 Claims, No Drawings

METHOD AND COMPOSITION FOR INHIBITING ARTERIOSCLEROSIS

This is a divisional of application Ser. No. 10/275,553 filed Nov. 7, 2003 now abandoned, which is a §371 National Stage Application of PCT Application No. PCT/JP01/03862 filed May 9, 2001, the disclosure of which is incorporated herein by reference.

TECHNICAL FIELD

The present invention relates to a method for achieving a potentiated effect of inhibiting arteriosclerosis expressed through the concomitant use of a drub having cholesterol-lowering activity, for example a hydroxymethylglutaryl-CoA reductase inhibitor (hereinafter referred to as a statin), and a reduced coenzyme $Q_{10}$ occurring in plasma low-density lipoprotein (hereinafter referred to a LDL) and having LDL antioxidant activity and to a composition therefor.

BACKGROUND ART

Coronary arterial disease is one of the diseases deserving the utmost attention today. It is suspected that a variety of factors contribute in a complex way to arteriosclerosis which triggers coronary arterial disease but an increased blood level of cholesterol is a major factor and the more direct factor is the increase and oxidative degeneration of low-density lipoprotein (LDL) which comprises cholesterol particles.

For the prevention of arteriosclerosis, it is important to lower the blood cholesterol level. Statins reportedly produce marked cholesterol lowering effects in patients with hypercholesterolemia. Statins inhibit hydroxymethylglutaryl-CoA reductase, the rate-determining enzyme in cholesterol biosynthesis, to thereby interfere with cholesterol biosynthesis and through the consequent reduction in intrahepatic cholesterol content and ensuing increase in LDL receptors, lower the plasma cholesterol level. However, notwithstanding the fact that it is about a decade since this drub was developed, thee has been reportedly no change in the incidence of conronary arterial disease and it is, thus, insufficient to merely lower cholesterol alone for the inhibition of arteriosclerosis.

Regarding the etiologic mechanism of arteriosclerosis, the LDL oxide hypothesis is known. Thus, it is postulated that LDL is oxidized to ox-LDL, which is taken up in macrophages and the resulting foam cells are deposited on the arterial wall to cause progression of arteriosclerosis. Recent years have seen many research results endorsing this hypothesis. The antiarteriosclerotic effect of the antihyperlipidemic drug probucol is considered to arise from its antioxidant activity, not from its cholesterol-lowering activity. Thus, for the inhibition of arteriosclerosis, not only depression of the cholesterol level but also inhibition of the oxidation of LDL can be an effective means.

As a natural antioxidant occurring in LDL, coenzyme $Q_{10}$ and vitamin E are known. Heretofore, in view of its abundant occurrence in LDL, vitamin E was once considered to be a central substance of antioxidant activity but recent studies have revealed that coenzyme $Q_{10}$ is a more important factor. While coenzyme $Q_{10}$ is a molecule synthesized in vivo, it is well known that its biosynthetic pathway involves hydroxymethylglutaryl-CoA as does the biosynthetic pathway of cholesterol and, therefore, the biosynthesis of coenzyme $Q_{10}$ is also inhibited by said statins. Actually many cases have been reported in which the administration of a statin caused depressions in the plasma coenzyme $Q_{10}$ level. Moreover, the administration of a statin reportedly rendered LDL more susceptible to oxidation and, therefore, the influence of a statin on coenzyme $Q_{10}$ and, hence, on the oxidizability of LDL has been suspected. To deal with the above decrease in coenzyme $Q_{10}$ caused by the administration of statin, attempts have been made to compensate for the decrease by administering coenzyme $Q_{10}$ (JP-A 02-233611, U.S. Pat. No. 5,082,650, U.S. Pat. No. 5,316, 765).

Coenzyme $Q_{10}$ occurs in two forms, the oxidized form and the reduced form, and it is known that, in the living body, usually about 40 to 90% of the coenzyme exists in the reduced form. It is the reduced coenzyme $Q_{10}$ that exhibits antioxidant activity within LDL particles and regardless of how large its amount is, the oxidized coenzyme $Q_{10}$ does not expresses antioxidant activity at all. Therefore, for the inhibition of arteriosclerosis, it is necessary to increase the reduced coenzyme $Q_{10}$ in the plasma. However, in the above-mentioned administration of coenzyme $Q_{10}$, the oxidized coenzyme $Q_{10}$ (ubiquinone) is invariably used.

SUMMARY OF THE INVENTION

The present invention has for its object to provide a method and a composition for achieving a more efficient recovery of the antioxidant activity of plasma LDL, or even augmentation thereof, which has been depressed by the use of an antihyperlipidemic or cholesterol-lowering drug to thereby insure a potentiated antiarteriosclerotic efficacy.

The present inventors conducted intensive investigations to accomplish the above object and found that compared with the administration of oxidized coenzyme $Q_{10}$, the administration of the reduced coenzyme $Q_{10}$ causes a prominent increase in the plasma concentration of the reduced coenzyme $Q_{10}$. The present invention has been accordingly accomplished.

The present invention, therefore, relates to a method for inhibiting arteriosclerosis, which comprises using a combination of a cholesterol-lowering agent and the reduced coenzyme $Q_{10}$ represented by the following formula (1).

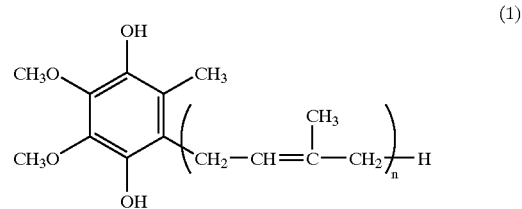

(1)

The present invention further relates to an antiarteriosclerotic composition comprising both of said cholesterol-lowering agent and said reduced coenzyme $Q_{10}$.

It is known to employ the oxidized coenzyme $Q_{10}$ for the purpose of compensating for the decrease in plasma coenzyme $Q_{10}$ concentration following administration of a statin. However, the use of the reduced coenzyme $Q_{10}$ according to the invention results in a marked elevation in the plasma concentration of the reduced coenzyme $Q_{10}$ as compared with the administration of the oxidized form and, therefore, is very effective in inhibiting oxidation of LDL and, hence, for the inhibition of arteriosclerosis.

The expression "inhibition of arteriosclerosis" as used in this specification means both prophylaxis for preventing arteriosclerosis and therapy for curing arteriosclerosis.

The present invention is now described in detail.

DISCLOSURE OF THE INVENTION

The method of inhibiting arteriosclerosis according to the present invention comprises using a cholesterol-lowering agent and the reduced coenzyme $Q_{10}$ in combination.

The cholesterol-lowering agent mentioned above is not particularly restricted but includes a hydroxymethylglutaryl-CoA reductase inhibitor (statin), a clofibrate antihyperlipidemic drug, a nicotinic acid derivative, a sterol derivative, elastase, a polyenephosphatidylcholine, melinamide, pantethine, icosapentanoic acid·EDTA, and so forth. However, among these, a hydroxymethylglutaryl-CoA reductase inhibitor is preferred.

The hydroxymethylglutaryl-CoA reductase inhibitor is not particularly restricted but includes lovastatin, simvastatin, pravastatin, atorvastatin, rosuvastatin, fluvastatin, cerivastatin, and pitavastatin, among others.

The ratio of the cholesterol-lowering agent to the reduced coenzyme $Q_{10}$ is not particularly restricted but is preferably 1:10 to 10:1 by weight, more preferably 1:5 to 5:1 by weight.

In the method of the invention, the cholesterol-lowering agent and the reduced coenzyme $Q_{10}$ are preferably administered both orally, and the dosage based on the reduced coenzyme $Q_{10}$ is preferably 10 mg to 1 g, more preferably 50 to 500 mg, in this oral regimen.

In the method of the invention, the cholesterol-lowering agent and the reduced coenzyme $Q_{10}$ may be administered at staggered times or concurrently. In the concurrent administration, the cholesterol-lowering agent and the reduced coenzyme $Q_{10}$ may be administered as a single preparation comprising the two active agents or each as an independent preparation. Furthermore, the start of administration of the reduced coenzyme $Q_{10}$ may either precede or follow the start of administration of the cholesterol-lowering agent or may be simultaneous.

The technology of providing said reduced coenzyme $Q_{10}$ is not particularly restricted but may for example comprise preparing coenzyme $Q_{10}$ by the known method, such as chemical synthesis, fermentation, or extraction from a naturally-occurring material, and concentrating the eluate containing the reduced coenzyme $Q_{10}$ by chromatography. Another version of the technology comprises adding a conventional reducing agent, such a sodium borohydride, sodium dithionite (sodium hydrosulfite) or the like, to above coenzyme $Q_{10}$ to reduce the oxidized coenzyme $Q_{10}$ to the reduced coenzyme $Q_{10}$ occurring in said coenzyme $Q_{10}$ in the routine manner and concentrating the same by chromatography. The objective coenzyme $Q_{10}$ can also be obtained by permitting said reducing agent to act on the available high-purity coenzyme $Q_{10}$.

The antiarteriosclerotic composition of the present invention is provided by formulating said reduced coenzyme $Q_{10}$ and a cholesterol-lowering agent.

The cholesterol-lowering agent is not particularly restricted but is preferably a hydroxymethylglutaryl-CoA reductase inhibitor (a statin).

The formulating ratio of the cholesterol-lowering agent to the reduced coenzyme $Q_{10}$ is not particularly restricted but is preferably 1:10 to 10:1, more preferably 1:5 to 5:1, by weight.

The composition of the invention may be supplemented with other pharmaceutically acceptable formulating agents in suitable amounts in the routine manner. Such pharmaceutical formulating agents are not particularly restricted but include excipients, disintegrators, lubricants, binding agents, antioxidants, coloring agents, anticoagulants, absorption promoters, solubilizers for active ingredients, stabilizers, and so on.

The excipient mentioned above is not particularly restricted but includes sucrose, lactose, glucose, cornstarch, mannitol, crystalline cellulose, calcium phosphate, and calcium sulfate, among others.

The disintegrator mentioned above is not particularly restricted but includes starch, agar, calcium citrate, calcium carbonate, calcium hydrogen carbonate, dextrin, crystalline cellulose, carboxymethylcellulose and tragacanth, among others.

The lubricant mentioned above is not particularly restricted but includes, talc, magnesium stearate, polyethylene glycol, silica and hydrogenated vegetable oil, among others.

The binding agent mentioned above is not particularly restricted but includes ethylcellulose, methylcellulose, hydroxypropylmethylcellulose, tragacanth, shellac, gelatin, gum arabic, polyvinylpyrrolidone, polyvinyl alcohol, polyacrylic acid, polymethacrylic acid and sorbitol, among others.

The antioxidant mentioned above is not particularly restricted but includes ascorbic acid, tocopherol, vitamin A, carotene, sodium hydrogen sulfite, sodium thiosulfate, sodium pyrosulfite and citric acid, among others.

The coloring agent mentioned above is not particularly restricted but includes the authorized coloring agent for addition to pharmaceutical products.

The anticoagulant mentioned above is not particularly restricted but includes stearic acid, talc, light silicic anhydride and silicic acid hydrate, among others.

The absorption promoter mentioned above is not particularly restricted but includes higher alcohols, higher fatty acids, and surfactants such as glycerol fatty acid esters, among others.

The above-mentioned solubilizer for active ingredients is not particularly restricted but includes benzoic acid, sodium benzoate, ethyl p-hydroxybenzoate, and so forth.

The usual dosage for an oral antiarteriosclerotic composition of the invention is preferably 10 mg to 1 g, more preferably 50 to 500 mg, based on coenzyme $Q_{10}$.

The composition of the invention can be provided in a variety of dosage forms. For example, soft capsules can be produced by adding or dissolving the reduced coenzyme $Q_{10}$ and the cholesterol-lowering agent in natural oil, an oily higher fatty acid, a higher fatty acid monoglyceride, or a mixture thereof and filling a soft capsule shell with the resulting oily product. In this case, any of gelatin-based capsule materials and capsule materials based on other water-soluble polymers can be employed. The capsules include microcapsules as well.

BEST MODE FOR CARRYING OUT THE INVENTION

The following examples and pharmaceutical production examples illustrate the present invention in further detail without defining the scope of the invention.

EXAMPLE 1

The effect of the reduced coenzyme $Q_{10}$ and the oxidized coenzyme $Q_{10}$ on the plasma level of the reduced coenzyme $Q_{10}$ in hamsters on high-fat diet Hamsters were fed on a high-fat diet containing 1.5% of cholesterol for one week and, then, a 1% (w/v) solution of either the oxidized or the reduced coenzyme $Q_{10}$ in olive oil was administered orally for 4 consecutive days. After overnight fasting, the plasma was collected and the reduced coenzyme $Q_{10}$ in the plasma was assayed by HPLC.

TABLE 1

Plasma level of the reduced coenzyme $Q_{10}$ (n = 3)

| Treatment | Gain in reduced coenzyme $Q_{10}$ in plasma (ng/ml) |
|---|---|
| Administration of oxidized coenzyme $Q_{10}$ | 10.1 (100%) |
| Administration of reduced coenzyme $Q_{10}$ | 14.4 (143%) |

It can be seen from Table 1 that compared with the group given the oxidized coenzyme $Q_{10}$, the plasma level of reduced coenzyme $Q_{10}$ was elevated more prominently in the group given the reduced coenzyme $Q_{10}$.

EXAMPLE 2

Evaluation of the antioxidant activity of plasma low-density lipoprotein (LDL) in hamsters on high-fat diet Hamsters were fed on a high-fat diet containing 1.5% of cholesterol for 1 week and, then, dosed orally with a 1% (w/v) solution of either the oxidized or the reduced coenzyme $Q_{10}$ in olive oil and 10 mg of pravastatin per kg body weight for 4 consecutive days. After overnight fasting, the plasma was collected, the plasma LDL was separated by density-gradient centrifugation method, and as a marker of LDL antioxidant activity, the lag time was measured. The lag time is defined herein as the value found by adding a copper ion (1 $\mu$M) to LDL (40 $\mu$g protein/mL) and monitoring at 234 nm the time course of conjugated diene structure of oxidized fat/fatty acid resulting from oxidation to determine the time interval until a sharp increase had begun in the conjugated diene concentration. The results are shown in Table 2.

TABLE 2

LDL antioxidant activity (n = 3)

| Treatment | Lag time (min) |
|---|---|
| Solvent control | 17 ± 4 |
| Administration of oxidized coenzyme $Q_{10}$ | 25 ± 8* |
| Administration of reduced coenzyme $Q_{10}$ | 44 ± 9** |

*P < 0.05, *P < 0.01, Student's t-test

It can be seen from Table 2 that while administration of the oxidized coenzyme $Q_{10}$ enhanced the antioxidant activity of LDL, administration of the reduced coenzyme $Q_{10}$ led to a greater enhancement in the LDL antioxidant activity.

PHARMACEUTICAL EXAMPLE 1

An encapsulated pharmaceutical product containing a hydroxymethylglutaryl-CoA reductase inhibitor and the reduced coenzyme $Q_{10}$ was manufactured according to the following formula.

Pravastatin 20 mg weight parts

Reduced coenzyme $Q_{10}$ 50 mg weight parts

Lactose 200 mg weight parts

Magnesium stearate 5 mg weight parts

INDUSTRIAL APPLICABILITY

By using the method and composition of the invention, the plasma level of the reduced coenzyme $Q_{10}$ can be remarkably elevated to potentiate LDL antioxidant activity, leading to excellent antiarteriosclerotic efficacy.

What is claimed is:
1. A method for enhancing LDL antioxidant activity which comprises administering to a subject a combination of a cholesterol-lowering agent and a reduced coenzyme Q10 represented by the following formula (1):

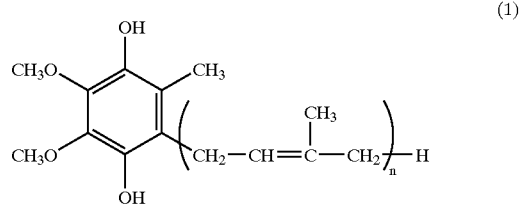

in the formula, n is 10;

wherein a ratio of the cholesterol-lowering agent to the reduced coenzyme Q10 is 1:10 to 10:1 by weight.
2. The method according to claim 1, wherein the cholesterol-lowering agent is a hydroxymethylglutaryl-CoA reductase inhibitor.